United States Patent [19]

Ericcson et al.

[11] Patent Number: 5,028,529

[45] Date of Patent: Jul. 2, 1991

[54] METHOD AND DEVICE FOR PRODUCING VARYING CONCENTRATION PATTERNS OF CHEMICALLY OR BIOLOGICALLY ACTIVE SUBSTANCES

[75] Inventors: Magnus Ericcson, Stockholm; Anne Bolmström, Åkersberga, both of Sweden

[73] Assignee: AB Biodisk, Solna, Sweden

[21] Appl. No.: 436,089

[22] Filed: Nov. 9, 1989

Related U.S. Application Data

[63] Continuation of Ser. No. 717,138, Mar. 28, 1985, abandoned.

[30] Foreign Application Priority Data

Apr. 3, 1984 [SE] Sweden .................... 8480107

[51] Int. Cl.⁵ ................... C12Q 1/24; C12Q 1/02
[52] U.S. Cl. ..................... 435/30; 422/55; 422/57; 435/4; 435/7.1; 435/29; 435/40; 435/287; 435/292; 435/300; 435/805; 436/518; 436/528
[58] Field of Search ............. 435/4, 7, 29, 30, 40; 422/57; 436/518, 528

[56] References Cited

U.S. PATENT DOCUMENTS

| | | | |
|---|---|---|---|
| 3,245,882 | 4/1966 | Guthrie | 422/55 |
| 3,455,788 | 7/1969 | Curry et al. | 435/293 |
| 3,509,026 | 4/1970 | Sanders | 435/33 |
| 3,510,263 | 5/1970 | Hach . | |
| 3,791,930 | 2/1974 | Saxholm | 435/33 |
| 3,932,223 | 1/1976 | Bucalo . | |
| 4,054,490 | 10/1977 | Vesterberg . | |
| 4,353,988 | 10/1982 | Couse et al. | 435/293 |
| 4,514,495 | 4/1985 | Schalkowsky et al. . | |

FOREIGN PATENT DOCUMENTS 2264089 10/1975 France .
WO82/02251 7/1982 World Int. Prop. O. .

*Primary Examiner*—Sam Rosen
*Attorney, Agent, or Firm*—Burns, Doane, Swecker & Mathis

[57] ABSTRACT

A method and a device for producing predetermined and defined varying concentration patterns of chemically or biologically active substances in chemical or biological qualitative or quantitative determinative methods, the method comprising application of the substance(s) within part of or the whole of a rectangular area of a medium in a concentration pattern having at least one concentration maximum and one concentration minimum: the device comprising a rectangular carrier on which the substance(s) have been applied so that the concentration pattern(s) thereof exhibit at least one concentration maximum and one concentration minimum.

19 Claims, 2 Drawing Sheets

METHOD AND DEVICE FOR PRODUCING VARYING CONCENTRATION PATTERNS OF CHEMICALLY OR BIOLOGICALLY ACTIVE SUBSTANCES

This application is a continuation of application Ser. No. 06/717,138, filed Mar. 28, 1985, now abandoned.

This invention relates to a method and a device for producing varying concentration patterns of chemically or biologically active substances.

The assay of chemically or biologically active substances in body fluids, for example blood, liquor, pus, sputum, secretion, bladder content or urine, is very essential in monitoring therapeutic treatment with such substances. With such a treatment, it is of critical importance to achieve therapeutic concentrations of the substance in question and to prevent a toxic concentration from being exceeded. Further, there is a great demand for the quantification of chemically or biologically active substances in various biologic materials, for example soil, cell cultures, allergen extracts and other cell extracts.

One of the methods of determining chemically or biologically active substances quantitatively in body fluids is the microbiologic method, i.e. it is based on the capacity of an active substance to promote or to inhibit growth of a suitable indicator microorganism. A well known method in this respect is the so-called paper disc method, which has been described a.o. by Jalling et al., Europ. J. Clin. Pharmacol. 4, 150–157 (1972). This method is based on a number of paper discs being impregnated with different amounts, representing different concentrations of a reference substance, for example an antibiotic. The sample containing the same active substance, which is to be assayed, is also impregnated onto a paper disc of the same kind. All of these paper discs, references with defined, varying concentrations, and samples with unknown concentrations are applied onto the surface of a culture medium, which has been inoculated with a selected microorganism. Distinct inhibition zones are formed around the reference discs as well as the discs impregnated with samples. The diameters of the inhibition zones around the reference discs are plotted against the concentrations to form a standard curve. The concentration corresponding to the zone diameter of the sample is then interpolated from the plotted standard curve. This method involves certain drawbacks such as a high number of discs to be tested on the same test plate, and that a new standard curve must be established on each test occasion.

Concentrations of enzymes and antigens are determined in an analogous manner using immunodiffusion methods, which have been described a.o. by OUCHTERLONY, Ö. & NILSSON, L.-Å.: Immunodiffusion and immunoelectrophoresis, I: Handbook of Experimental Immunology. Ed. D. M. Weir, Blackwell, Oxford, 2nd ed. (1973) and MANCINI, G., CARBONARA, A. O. & HEREMANS, J. F.: Immunochemical quantitation of antigens by single radial immunodiffusion, Immunochemistry 2 (1965) p. 235. In these techniques, the diffusion layer may consist, for example, of a thin layer of agargel containing a substrate specific for the enzyme to be determined or an antiserum or antibodies specific for the antigen to be determined. The enzyme or antigen is applied to the substrate in round holes, i.e. solutions are filled into wells made in the agar layer. The enzyme or antigen diffuses out radially from the diffusion centre, i.e. the well containing the solution. The reference wells containing defined varying concentrations of the enzyme or antigen, and the well containing the sample with an unknown concentration are tested on the same agargel plate.

The circular zone around an enzyme well can consist of a transparency in the otherwise turbid gel layer, for example in the assay of protease concentration in an agargel containing casein. The circular zone around an antigen well can consist of a precipitate in the otherwise clear gel layer. Reading and interpretation of results are similar to those described for the microbiologic test. The diameter (or area) of the zone around the unknown sample is read against a standard curve based on the diameters (or areas) around the reference wells.

Another immunodiffusion technique used for determining antigens or antibodies is "double diffusion (Ouchterlony) precipitation". Antigen as well as antibodies are filled in wells and allowed to diffuse toward each other. Where these substances meet in optimal proportions in the gel, a precipitate line will appear. The relative position of the line is related to the absolute concentration of the antigen or antibody in the respective wells, and its molecule size and rate of diffusion through the gel.

These methods have similar drawbacks as those of the microbiologic test. Moreover, these tests are time consuming since the large molecules involved diffuse slowly. The point of stationary equivalence is established after a long period of diffusion. The accuracy of results will be affected by the instability of concentration gradients unless readings are made at suitable times.

The sensitivity of microorganisms, for example bacteria, towards a biologically or chemically active substance is at present determined by measuring the minimum inhibitory concentration (MIC). MIC determinations by available methods are complicated, time consuming and expensive. Two different methods are essentially used today for determining MIC values. One of the methods comprises a series of two-fold dilutions of the active substance in a fluid or solid medium. This method has the disadvantage of giving less precise and less accurate information on the sensitivity of a microorganism because it is based on a discontinuous set of dilutions. The other method is based on the diffusion of the active substance from a defined diffusion centre in an agar layer. The concentration gradients of different substances depend on the particular diffusion properties of the individual substances. Therefore for each substance a regression line correlating the logarithm of MIC values (determined by the dilution method) to inhibition zone diameters around a disc containing a defined amount of the substance, must be established for different groups of bacteria (Ericsson, H. M. & Sherris, J. C., Antibiotic Sensitivity Testing, Acta Path. & Microbiol. Scand., Section B 1971, Supplement No. 217).

The disadvantages of the aforementioned methods can be eliminated by the present invention, whereby the substance or substances, of which the activity against microorganisms or other biologic cells, or the concentration of which is to be measured, are applied in defined amounts within a rectangular area on the surface of a medium, containing chemical or biologic material reacting with the substance or substances, in such a manner that the substance or substances in the entire area or in parts thereof are present in a predetermined concentration pattern, having at least one concentration maximum and one concentration minimum, and that at least one of these minima/maxima is preferably located at the end of the aforementioned rectangular area.

Further objects and advantages of the present invention will be better understood by carefully reading the following description of the presently preferred exemplary embodiments of the invention in conjunction with the accompanying drawings of which:

Figure 1:
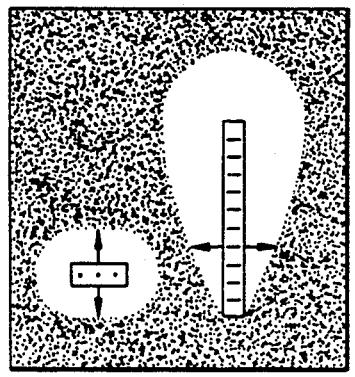
FIG. 1 illustrates one embodiment of a device according to the present invention, where the substance is applied or the entire surface of the carrier with a concentration gradient decreasing from a maximum at one end of the carrier to a minimum at the other end, where the sample is applied to a unit.

According to the invention, the medium can be a culture medium, e.g. a layer of agar or some other polymer containing suitable growth factors when required, or the medium may be a diffusion layer and/or a reaction layer.

The chemical or biologic material in the medium can be, for example microorganisms, other biologic cells, antiserum, antibodies or enzyme substrates.

The biologically or chemically active substances are, for example, antimicrobial substances, microbioligically active substances, substances having an inhibitory, lethal, toxic or mutagenic effect on cells.

The substance or substances can be applied so that the concentrations thereof in the rectangular area and respectively on the carrier is highest in the centre and decreases towards the two ends, or that the concentration is highest at one end of the rectangular area and decreases towards the other end. Further, the concentration of a first substance can be uniformly distributed over the rectangular area, and respectively carrier, while a second substance is present with a concentration gradient decreasing from one end to the other. A first substance may also have a concentration gradient in the rectangular area, and respectively carrier, decreasing from one end to the other, while a second substance is applied with a concentration gradient decreasing in a direction opposite to the gradient of the first substance. The substance or substances may also be applied in the rectangular area, and respectively on the carrier, in such a way that several concentration maxima and minima are found in the aforesaid area and respectively carrier.

A substance also may be applied on a portion of the rectangular area, and respectively carrier, with the concentration decreasing from one end of the rectangle to the other, and in the portion of the area and respectively carrier, free from substance, a sample the concentration of which is to be determined, is applied.

A specific concentration pattern in a medium may be attained, for example by applying a rectangular carrier, on which the substance or substances prevail in the desired concentration pattern, to the surface of the medium or vice-versa. A specific concentration pattern can also be attained by applying a number of units, which contain the substance or substances in known concentrations, to the surface of a medium in such a way, that the specific concentration pattern is obtained in the rectangular area.

Examples of carriers suitable for use in the present invention are thin sheets of neutral, substantially nonporous material, for example cellulose, polyacrylamide, polyester, polyamide or similar material These materials can be opaque or transparent.

The culture medium can also be applied in the form of a thin layer of a dehydrated medium on the carrier, for example of the type described in the international patent application PCT/US 82/00085 (publication No. WO 82/02563).

In one embodiment of a device according to the present invention, the substance is applied on the entire surface of the carrier with a concentration gradient decreasing from a maximum at one end of the carrier to a minimum at the other end. The substance can be applied in a manner known per se, for example by micropipetting specific volumes of reference solutions having defined decreasing concentrations onto the surface of the carrier, at certain intervals from each other, resulting in a continuous concentration gradient along the carrier. When the concentration of a substance in a body fluid is to be determined for example, a sample thereof can be pipetted onto a unit, which is then applied to the surface of a culture medium which has been inoculated with a selected microorganism. The rectangular carrier with a concentration gradient of the reference substance is simultaneously applied to the same test plate, which is then incubated in the usual manner. Along the rectangular carrier a drop-shaped inhibition zone is formed where growth of the microorganism is inhibited. The width of the zone is largest at the end of the carrier where the highest concentration of the reference substance is to be found and tapers accordingly along the decreasing concentration gradient towards the end of the carrier where the lowest concentration of the reference substance is located. An inhibition zone is also formed around the unit containing the sample. This is illustrated in FIG. 1.

The width of the zone around the sample unit is measured and compared to the width of the drop-shaped zone along the concentration gradient of the reference, whereby the unknown concentration can be interpolated as indicated by arrows in FIG. 1. To facilitate a direct reading of the concentration, the rectangular carrier is preferably graded with a concentration scale.

Figure 2:
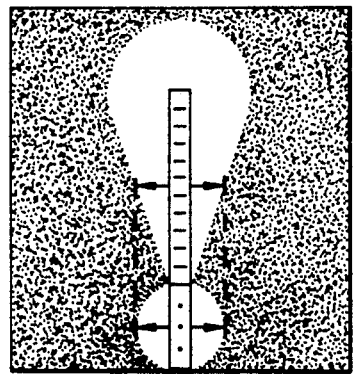
FIG. 2 illustrates another embodiment of a device according to the present invention, where the reference substance is applied to a portion of the carrier with a concentration gradient decreasing from a maximum at one end of the carrier where the sample is applied to a portion of the carrier free from the reference substance.

In another embodiment of a device according to the present invention, the reference substance is applied on a portion of the carrier with a concentration gradient decreasing from a maximum at one end of the carrier. A sample of the body fluid containing the substance, the concentration of which is to be determined, is applied by means of a micropipette onto the portion of the rectangular carrier free from reference substance. The carrier is preferably graded with a scale for direct reading of the concentration. The carrier after application of the unknown sample, is applied onto the surface of a culture medium, previously inoculated with a selected microorganism. The test is then carried out in the usual manner. A drop-shaped inhibition zone is formed where no growth of microorganism occurs around the rectangular carrier, and an inhibition zone is formed around the carrier where the test sample had been applied (see FIG. 2). This form of the device allows a direct reading of the concentration in the sample, by a comparison of the width of the zone around the sample to the width of the drop-shaped zone along the concentration gradient of the reference.

These two embodiments can be used in an analogous way for the assay of enzymes, antigens and growth promoting substances, such as vitamins, where the drop-shaped zone along the concentration gradient of the reference and the zone around the sample may consist of a transparency or precipitate or growth of microorganisms in contrast to inhibition of growth.

In a biochemical analysis, for example of the nitrate content in soil using the enzyme nitrate reductase, the reference substrate is applied on a portion of the carrier surface with a concentration gradient decreasing from a maximum at one end of the carrier. A sample of the soil containing nitrate, the concentration of which is to be determined, is applied by means of a micropipette onto the portion of the rectangular carrier free from the reference substance. The carrier is preferably graded with a scale for a direct reading of the concentration. A defined amount of the specific enzyme which reacts with the nitrate is applied uniformly on the entire surface of the carrier. Suitable reagents, for example sulphanilic acid and N,N-dimethyl-1-naphtylamine, which can show this enzyme-substrate reaction in the form of a colour change are applied onto the entire carrier surface, or is present as an integrated part of the carrier. The intensity of the colour of the sample is compared to the range of varying colour intensities along the calibrated portion of the carrier consisting of a concentration gradient of the reference substrate.

These two aforementioned embodiments can preferably be used a.o. for the determination of unknown concentrations of active substances in different samples.

In yet another embodiment of the device according to the present invention, a first substance is applied in a concentration uniformly distributed over the rectangular carrier, while a second substance is applied in a concentration gradient decreasing from one end to the other end of the carrier.

Figure 3:
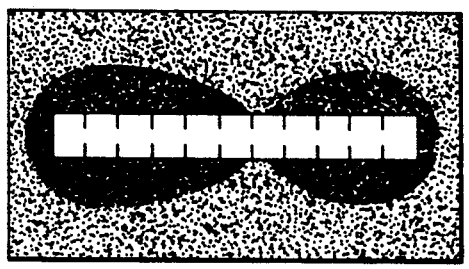
FIG. 3 to FIG. 6 illustrates the interaction between two antibiotics A and B, which are applied to the same carrier, the concentration gradients of which decrease in opposite directions.
Figure 4:
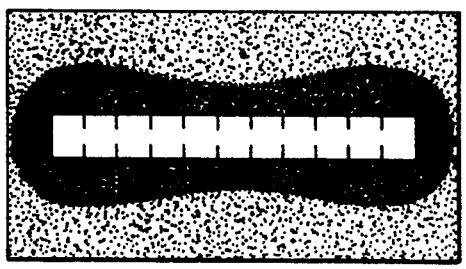
Figure 5:
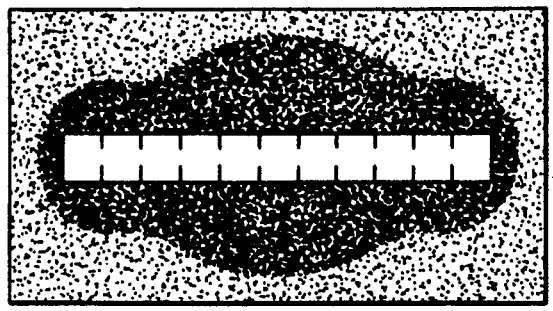
Figure 6:
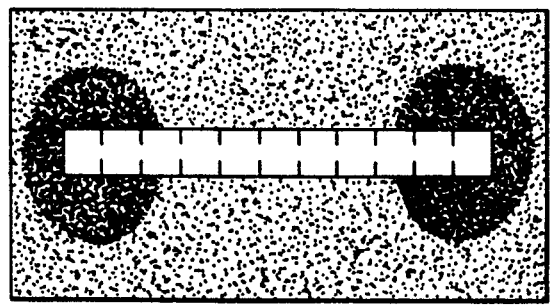

In a further embodiment of the device according to the invention, a first substance is applied in a concentration gradient decreasing from one end of the carrier to the other, while a second substance is applied in a concentration gradient which decreases in a direction opposite to the gradient of the first substance. The concentration of the first substance is thus highest where the concentration of the second substance is lowest, and vice-versa. This embodiment of the device can be used to study the interaction between different substances, for example the binding of antimicrobial substances to proteins, the combined action of antibiotics resulting in additive effects, synergism or antagonism. FIGS. 3–6 illustrate the interaction between two antibiotics A and B, which are applied on the same carrier, the concentration gradients of which decrease in opposite directions as described above. After application of the device on an inoculated medium, and after incubation inhibition zones of varying shapes will be obtained. In FIG. 3, two drop-shaped zones on opposite ends indicate that substances A and B act independently of each other. In FIG. 4, the ends of the otherwise drop-shaped zones instead of tapering towards the edge of the carrier, merge into a common inhibition zone, indicating an additative effect. In FIG. 5, the ends of the otherwise drop-shaped zones merge into a common inhibition zone which is larger than the zones at either end of the carrier, indicating a synergistic effect. In FIG. 6, the edges of the otherwise drop-shaped zones abruptly transect the carrier edge, instead of gradually tapering towards it, indicating an antagonistic effect.

The aforementioned embodiments are suitable for use, for example in determining the concentration ranges and proportions between two or more substances interacting in an additive, synergistic or antagonistic manner. This invention provides a simple means of determining the optimal ratios of two or more substances to be administered together in guiding the therapy with a combination of drugs, e.g. antibiotics, antimycotics and cytostatic drugs.

Figure 7A:
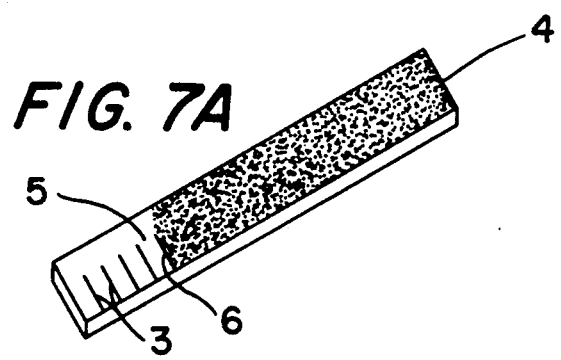
FIG. 7 illustrates one embodiment of a device according to the invention comprising a transparent or opaque carrier with a printed scale.
Figure 7B:
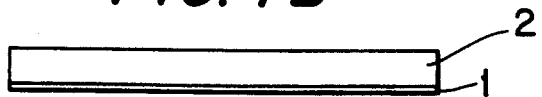

FIG. 7 shows a schematic illustration of one embodiment of a device according to the invention comprising a transparent or opaque carrier 1, with a printed scale 3 indicating the concentrations of the active substance or other related parameters thereof. On the carrier, a predetermined concentration pattern of an active substance has been applied. 2 is a growth medium and/or diffusion layer and/or other reaction layer that has been inoculated with a microorganism or other biological or biochemical indicator which interacts with the active substance on the carrier. 4 is the zone of growth of the microorganism or other visible biological or biochemical reaction. 5 is the zone of inhibition or growth of a microorganism or zone of other reaction/no reaction for other indicator systems. 6 is the border between the zones of growth/inhibition for a microorganism or other visible reaction/no reaction or other two discriminatory reactions for other indicator systems. The concentration of the active substance or other parameters related thereof which is associated with the inhibition of growth, i.e. MIC (minimum inhibitory concentration) or other characteristic reaction, can be easily read directly on the device.

For the determination of the minimum inhibitory concentration (MIC) and the minimum bactericidal concentration (MBC), the latter of which is the lowest concentration of an antimicrobial substance inhibiting visible growth of microorganisms in an irreversible manner, i.e. killing of the inoculum under a set of defined test conditions, a rectangular carrier of the kinds earlier described can be used, whereby the MIC value or related parameter thereof can be read directly as the growth/inhibition border (6 in FIG. 7) on the carrier or as the point where the tapering border of the drop-shaped zone along the carrier transects the edge of the carrier. The MBC value can be subsequently determined by replacing the carrier containing the antimicrobial substance, around which a drop-shaped zone has been formed, with a new carrier containing suitable inactivating substance, for example enzymes or other chemicals which can effectively inactivate the residual antimicrobial substance in the culture medium. After additional incubation in an antimicrobial free medium the size and shape of the drop-shaped zone, or the position of the growth/inhibition border on the carrier as in FIG. 7, will change in relation to the MBC value.

The method and the device according to the present invention, can thus be used, for example to characterize the sensitivity or other property of microorganisms and other biologic cells to antimicrobial substances, and respectively to substances which may have an inhibitory, lethal, toxic, mutagenic or growth promoting effect on the cells. The method and device can also be used to quantify biologically or biochemically active substances and substrate-specific enzymes or enzyme-specific substrates, to assess the cancerogenic, mutagenic or toxic effects of different substances and to select mutants of microorganisms or other biologic cells resistant to antimicrobial agents or other drugs or dependant on different growth factors.

The term "microorganism" refers to bacteria, such as the enterobacteriaceae, staphylococci, streptococci, hemofilus, neisseriaceae, bacteroides, and clostridia, mycobacteria, actinomyces, mycoplasma, nocardia, virus, and fungi such as moulds, yeasts and candida.

The term "biologic cells" comprises cancer cells, normal human cells, animal cells and plant cells, of the type "stem cells".

Antimicrobial substances are antibiotics, for example aminoglycosides, $\beta$-lactam antibiotics, macrolide antibiotics, polymyxins, polypeptides and other chemotherapeutics such as sulfonamides, antimycotics, for example 5-fluorocytosine, amphotericin, antiviral agents such as adenine arabinoside (Ara-A), trifluorothymidine, antituberculous drugs, such as isoniazide and cycloserine, and disinfectants, antiseptics and preservatives such as chlorohexidine, ethanol and benzalkonium chloride.

Substances which may have an inhibitory, lethal, toxic or mutagenic effects on cells are anticancer agents, for example anthracyclines, mitomycins, cancerogenic/mutagenic substances such as dimethylnitrosamine, herbicides such as paraquat and pesticides and insecticides such as dicophane (DDT).

Microbiologically active substances are, in addition to the afore mentioned antimicrobial substances, bacteriocins, for example colicins, different growth factors, such as amino acids, vitamins and other nutrients, different body fluids and components thereof such as serum, blood and specific components in serum, for example $\beta$-lysine.

Biologically active substances are interferons, such as human interferon HuIFN-$\beta$, IF4N-$\beta$, enzymes such as $\beta$-lactamases, proteases and ureases, enzyme specific substrates such as nitrates, $\beta$-lactam antibiotics, aminoglycosides and chloramphenicol, antigens such as immunoglobulins, polysaccharides and toxins from microorganisms.

What we claim is:

1. A test device for making a qualitative or quantitative determination comprising a substantially rectangular non-porous carrier containing on the surface thereof at least one gradient of at least one chemically or biologically active substance, wherein substantially all of the active substance is on the surface of the carrier, so that when the carrier is applied to the surface of a reaction medium, a concentration pattern is transferred to the surface of said reaction medium and a qualitative or quantitative determination of activity can be made.

2. The test device as claimed in claim 1 wherein the medium is a culture medium or a diffusion layer.

3. The test device as claimed in claim 1 wherein the medium is a culture medium.

4. The test device as claimed in claim 1 wherein the chemically or biologically active substance is an antimicrobial agent, a biological cell, an enzyme substrate, an enzyme, a chemical reagent, an antiserum, an antibody or an antigen.

5. The test device as claimed in claim 1 wherein the chemically or biologically active substance is an antimicrobial agent.

6. The test device as claimed in claim 1 wherein the chemically or biologically active substance has one gradient wherein the concentration is highest in the center of the carrier.

7. The test device as claimed in claim 1 wherein the chemically or biologically active substance has one gradient such that the concentration of the substance is highest at one end of the carrier and decreases as it approaches the opposite end of the carrier.

8. The test device as claimed in claim 1 wherein the chemically or biologically active substance has two gradients wherein the concentration of the first substance is highest at one end of the carrier and gradually decreases as said first substance approaches the opposite end of the carrier and wherein the concentration of the second substance is highest at the opposite end of the carrier and gradually decreases as it approaches the end of the carrier wherein the concentration of the first substance is the highest.

9. The test device as claimed in claim 1 wherein there are two chemically or biologically active substances on the carrier, wherein the first substance is applied in a uniform concentration over the entire carrier and the concentration of the second substance is highest at one end of the carrier and gradually decreases as it approaches the opposite end of the carrier.

10. A test device for making a qualitative or quantitative determination of antimicrobial activity comprising a substantially rectangular non-porous carrier containing on the surface thereof at least one gradient of at least one antimicrobial agent, wherein substantially all of the antimicrobial agent is on the surface of the carrier, so that when the carrier is applied to the surface of a medium containing a microorganism, a concentration pattern is formed on the surface of said medium and a qualitative or quantitative determination of antimicrobial activity can be made.

11. A method for producing a concentration pattern of at least one chemically or biologically active substance to allow a qualitative or quantitative determination to be made, said method comprising:

contacting a substantially rectangular non-porous carrier having at least one gradient of at least one chemically or biologically active substance on its surface to a medium such that a concentration pattern is transferred to said medium.

12. The method as claimed in claim 11 wherein the medium is a culture medium or a diffusion layer.

13. The method as claimed in claim 11 wherein the chemically or biologically active substance is an antimicrobial agent, a biological cell, an enzyme substrate, an enzyme, a chemical reagent, an antiserum, an antibody or an antigen.

14. The method as claimed in claim 11 wherein the chemically or biologically active substance is an antimicrobial agent.

15. The method as claimed in claim 11 wherein the chemically or biologically active substance has one gradient wherein the concentration is highest in the center of the carrier.

16. The method as claimed in claim 11 wherein the chemically or biologically active substance has one gradient such that the concentration of the substance is highest at one end of the carrier and decreases as it approaches the opposite end of the carrier.

17. The method as claimed in claim 11 wherein the chemically or biologically active substance has two gradients wherein the concentration of the first substance is highest at one end of the carrier and gradually decreases as said first substance approaches the opposite end of the carrier and wherein the concentration of the second substance is highest at the opposite end of the carrier and gradually decreases as it approaches the end of the carrier wherein the concentration of the first substance is the highest.

18. The method as claimed in claim 11 wherein there are two chemically or biologically active substances on the carrier, wherein the first substance is applied in a uniform concentration over the entire carrier and the concentration of the second substance is highest at one end of the carrier and gradually decreases as said second substance approaches the opposite end of the carrier.

19. A method for producing a concentration pattern of at least one antimicrobial agent to allow a qualitative or quantitative determination of antimicrobial activity to be made, said method comprising:

contacting a substantially rectangular non-porous carrier having at least one gradient of at least one antimicrobial agent on its surface to a medium containing a microorganism such that a concentration pattern is transferred to said medium.

* * * * *